United States Patent [19]

Beddell et al.

[11] 4,075,191
[45] Feb. 21, 1978

[54] BIOLOGICALLY ACTIVE AMIDES

[75] Inventors: Christopher Raymond Beddell, Ashford; Lawrence Alfred Lowe, Swanley; Samuel Wilkinson, Beckenham, all of England

[73] Assignee: Burroughs Wellcome Co., Research Triangle Park, N.C.

[21] Appl. No.: 625,386

[22] Filed: Oct. 24, 1975

[30] Foreign Application Priority Data

Oct. 25, 1974 United Kingdom ............... 46167/74

[51] Int. Cl.$^2$ .................... C07C 103/52; A61K 37/00
[52] U.S. Cl. .................... 260/112.5 LH; 260/112.5 R; 424/177
[58] Field of Search ............... 260/112.5 LH; 424/177

[56] References Cited
U.S. PATENT DOCUMENTS

| | | | |
|---|---|---|---|
| 3,853,834 | 12/1974 | Shields | 260/112.5 LH |
| 3,853,837 | 12/1974 | Fujino et al. | 260/112.5 LH |
| 3,880,825 | 4/1975 | Sakakibara et al. | 260/112.5 LH |

OTHER PUBLICATIONS

Fujino et al.: Biochem. Biophys. Res. Comm., 49, 863–869 (1972).
Monahan et al.: Biochem., 12, 4616–4620 (1973).
Fujino et al.: Biochem. Biophys. Res. Comm., 60, 406–412 (1974).
Yanaihara et al.: Biochem. Biophys. Res. Comm., 52, 64–73 (1973).
Vilchez-Martinez et al.: Biochem. Biophys. Res. Comm., 59, 1226–1232 (1974).
Fujino et al.: Biochem. Biophys. Res. Comm., 57, 1248–1256 (1974).
Coy et al.: Biochem. Biophys. Res. Comm., 57, 335–340 (1974).

Primary Examiner—Delbert R. Phillips
Attorney, Agent, or Firm—Donald Brown

[57] ABSTRACT

Novel peptide compounds of the formula

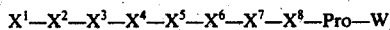

$X^1$—$X^2$—$X^3$—$X^4$—$X^5$—$X^6$—$X^7$—$X^8$—Pro—W are provided together with their acid addition salts and their complexes with pharmaceutically acceptable metals. The compounds are LH-RH analogues and together with their salts and complexes exhibit LH-RH antagonist activity.

In the formula
- $X^1$ is selected from pyroglutamyl, a group $V^1$-Pro- where $V^1$ is acyl, alkyloxycarbonyl or aralkyloxycarbonyl, and a group $V^2$—CO— where $V^2$ is cycloalkyl;
- $X^2$ is selected from histidyl and a direct bond;
- $X^3$ is selected from phenylalanyl optionally substituted in the benzene ring and tryptophyl;
- $X^4$ is selected from glycyl, seryl, alanyl (D- or L), D-leucyl and D-valyl;
- $X^5$ is phenylalanyl optionally substituted in the benzene ring;
- $X^6$ is selected from glycyl, alanyl (D- or L-), D-leucyl and D-valyl;
- $X^7$ is selected from phenylalanyl optionally substituted in the benzene ring and leucyl;
- $X^8$ is a direct bond when $X^2$ is histidyl and is otherwise arginyl or homoarginyl; and
- W is selected from glycine amide and a group —$NR^1R^2$ where $R^1$, $R^2$ and the nitrogen atom together comprise a group selected from amino, N-alkylamino, N,N-dialkylamino, pyrrolidino, morpholino and 1-methyl-5-aminomethyltetrazolyl, the 'alkyl' having from 1 to 4 carbon atoms and being optionally substituted by an hydroxyl group, provided that, when $X^1$, $X^3$, $X^4$, $X^5$, $X^7$ and $X^8$ are respectively pyroglutamyl, tryptophyl, seryl, tyrosyl, leucyl and arginyl, W is other than glycine amide or N-ethylamino when $X^6$ is glycyl and is other than glycine amide when $X^6$ is D-alanyl.

All references are to the L-amino acids and their radicals except in the case of glycine and unless otherwise stated.

Also provided are methods for the preparation of the peptides, salts and complexes, pharmaceutical formulations containing them and methods for the preparation of such formulations, and methods for the use of the peptides, salts and complexes in human and in veterinary medicine.

6 Claims, No Drawings

BIOLOGICALLY ACTIVE AMIDES

This invention relates to peptides, their acid addition salts and complexes of the peptides with pharmaceutically acceptable metals; to the preparation of such peptides, salts and complexes; to formulations containing such peptides, salts or complexes and the preparation of such formulations; and to the use of the peptides, salts and complexes in human and veterinary medicine.

More particularly the present invention relates to analogues of luteinizing hormone — releasing hormone (LH-RH), a decapeptide having the structure

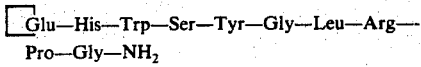

The abbreviations used herein for amino acids and their radicals are those conventional in the art and may be found in, for example, Biochemistry, 11, 1726 (1972). In the above and throughout the following all references are to the L-amino acids and their radicals except in the case of glycine and unless otherwise stated.

LH-RH is released from the mammalian hypothalamus into the veins of the hypothalamo-hypophyseal portal system and acts on the anterior pituitary to cause the release of two gonadotrophins, luteinizing hormone (LH) and follicle-stimulating hormone (FSH). LH stimulates the synthesis of steroid hormones in the gonads of both sexes and, in the female, also induces the ovulation of suitably matured ovarian follicles. FSH stimulates (in the female) the growth and maturation of ovarian follicles and (in the male) the growth of the seminiferous tubules and the early stages of spermatogenesis. The maturation of spermatozoa in the male is controlled by androgens whose formation is controlled by LH.

It has now been appreciated by the Applicants that if the sequence of LH-RH is written in the form:

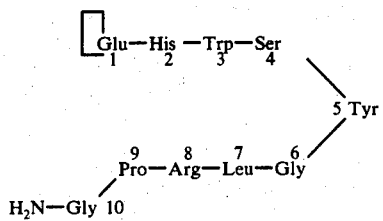

it is seen that the amino acids are symmetrically distributed about the tyrosine residue. The amino acids may be considered in the following pairs, tyrosine and glycine amide having no formal partners:-

| Pair | General Features |
|---|---|
| Ser, Gly | Small side chain, hydrophilic but neutral |
| Trp, Leu | Hydrophobic and neutral |
| His, Arg | Hydrophilic and basic |
| Glu, Pro | Medium side chain with 5-membered ring, character intermediate but neutral |

In view of the marked structural symmetry, it is not inconceivable that structural symmetry is evident in the active conformation and that the receptor possesses the same symmetry.

Consistent with this concept of symmetry of LH-RH and the receptor therefor, it has now been found that the asymmetric LH-RH analogues of formula (I)

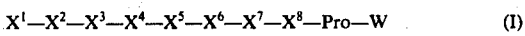

and acid addition salts thereof exhibit LH-RH antagonist activity in in vitro tests. As the term is used herein, an LH-RH antagonist is a compound which reduces the biological response to the natural hormone when the two are present together in a biological system. Thus the compounds of formula (I) and their acid addition salts effect a reduction in LH and FSH release when incubated with isolated rat anterior pituitary glands in the presence of LH-RH as compared with control results obtained with LH-RH alone present.

In formula (I), $X^1$ is selected from pyroglutamyl, a group $V^1$—Pro— where $V^1$ is acyl, alkyloxycarbonyl or aralkyloxycarbonyl, and a group $V^2$—CO— where $V^2$ is cycloalkyl;

$X^2$ is selected from histidyl and a direct bond;

$X^3$ is selected from phenylalanyl optionally substituted in the benzene ring and tryptophyl;

$X^4$ is selected from glycyl, seryl, alanyl (D- or L), D-leucyl and D-valyl;

$X^5$ is phenylalanyl optionally substituted in the benzene ring;

$X^6$ is selected from glycyl, alanyl (D- or L-), D-leucyl and D-valyl;

$X^7$ is selected from phenylalanyl optionally substituted in the benzene ring and leucyl;

$X^8$ is a direct bond when $X^2$ is histidyl and is otherwise arginyl or homoarginyl; and W is selected from glycine amide and a group —NR$^1$R$^2$ where R$^1$, R$^2$ and the nitrogen atom together comprise a group selected from amino, N-alkylamino, N,N-dialkylamino, pyrrolidino, morpholino and 1-methyl-5-aminomethyltetrazolyl, the 'alkyl' having from 1 to 4 carbon atoms and being optionally substituted by an hydroxyl group, provided that, when $X^1$, $X^3$, $X^4$, $X^5$, $X^7$ and $X^8$ are respectively pyroglutamyl, tryptophyl, seryl, tyrosyl, leucyl and arginyl, W is other than glycine amide or N-ethylamino when $X^6$ is glycyl and is other than glycine amide when $X^6$ is D-alanyl.

When $X^1$ is $V^1$—Pro— as above defined the acyl preferably has 2 to 4 carbon atoms (for example, acetyl) the 'alkyl' moiety in the alkyloxycarbonyl preferably has 1 to 4 carbon atoms (for example, isopropyl or t-butyl) and the 'aralkyl' moiety in the aralkyloxycarbonyl is preferably benzyl. When $X^1$ is $V^2$—CO— as above defined the group $V^2$ preferably has 3 to 7 carbon atoms in the ring, for example cyclopentyl.

The benzene ring of the phenylalanyl radical (radicals $X^3$, $X^5$ and $X^7$) may be substituted with one or more groups selected from alkoxy (e.g. methoxy), halogen (e.g. chlorine), alkyl (e.g. methyl), hydroxyl, nitro and amino; when only one substituent group is present this is preferably in the 4-position with respect to the remainder of the molecule.

As a sub-class within formula (I) are the compounds and the salts thereof wherein $X^1$ is pyroglutamyl, $V^1$—Pro— wherein $V^1$ is alkyloxycarbonyl carbonyl where the 'alkyl' has 1 to 4 carbon atoms, or $V^2$—CO— wherein $V^2$ is cycloalkyl having 3 to 7 carbon atoms in the ring;

$X^3$ is phenylalanyl or tryptophyl;

$X^4$ is alanyl (D- or L-) or seryl;

$X^5$ is phenylalanyl or tyrosyl;
$X^6$ is glycyl or alanyl (D- or L-);
$X^7$ is leucyl; and
W is glycine amide, N-alkylamino wherein the 'alkyl' has 1 or 2 carbon atoms, or 1-methyl-5-aminomethyltetrazolyl.

It will be appreciated by those skilled in the peptide art that those compounds and the salts thereof within formula (I) which do not include either or both of the seryl and tryptophyl radicals present significant advantages as regards ease of synthesis when compared both with LH-RH itself and with analogues thereof which include these radicals. An inherent difficulty with the introduction of the seryl radical is that the hydroxyl group therein must be protected if O-acylation is to be avoided. Thus two extra steps are required in any scheme involving introduction of seryl: protection and subsequent deprotection of the hydroxyl group, of which the former is typically a particularly laborious procedure. The tryptophyl radical readily oxidises, particularly in acid conditions commonly used in peptide synthesis for removal of protecting groups, to yield coloured by-products that are difficult to remove. As a consequence of this peptides such as LH-RH containing the tryptophyl radical are characteristically unstable, a disadvantage not shared by the compounds and salts of formula (I) which do not include this radical.

The activity of the compounds of formula (I) resides in the peptide and the acid in the acid addition salts is of less importance although for therapeutic purposes it is preferably pharmacologically and pharmaceutically acceptable to the recipient. Examples of such suitable acids include (a) mineral acids: hydrochloric, hydrobromic, phosphoric, metaphosphoric, nitric and sulphuric acids; (b) organic acids: tartaric, acetic, citric, malic, lactic, fumaric, benzoic, glycollic, gluconic, gulonic, succinic and arylsulphonic, for example p-toluenesulphonic acids.

The pharmaceutically and pharmacologically acceptable acid addition salts together with those salts which are not so acceptable (for example salts of hydrofluoric and perchloric acids) have utility in isolation and purification of the peptides, and of course the unacceptable salts are also valuable in the preparation of the acceptable salts by techniques well known in the art. Those peptides containing a plurality of free amino groups may be obtained in the form of mono- or poly- acid addition salts, or as mixed salts of a plurality of acids.

The compounds of formula (I) may be prepared by any of the methods known in the art for the preparation of compounds of analogous structure. Thus they may be formed by the sequential coupling of appropriate amino acids using either classical methods of peptide synthesis or solid phase procedures, or by the initial preparation and subsequent coupling of peptide subunits. Such reactions may be effected by, for example, activating the carboxylic acid group of the ingoing amino acid and protecting the non-reacting amino and carboxylic acid groups. Such techniques are standard in the peptide art. Details of suitable activating and protecting (masking) groups and of suitable reaction conditions (both for the coupling reactions and for the removal of protecting groups) giving the minimum of racemisation may be found in the following literature which is given purely by way of exemplification and which is intended to be neither exhaustive nor limiting.

a. Published United Kingdom patent specifications Nos. 1 042 087; 1 048 086; and 1 281 383.

b. Schröder and Lübke, "The Peptides" (Academic Press) (1965).

c. Bellean and Malek, J. Am. Chem. Soc., 90, 165 (1968).

d. Tilak, Tetrahedron Letters, 849 (1970).

e. Beyerman, Helv. Chim. Acta., 56, 1729 (1973).

f. Stewart and Young, "Solid Phase Peptide Synthesis" (W. H. Freeman and Co.) (1969).

The pyroglutamyl, arginyl and homoarginyl (Har) radicals may not only be incorporated into the compounds of formula (I) in the fashion described above but may also be formed in situ in the assembled polypeptide chain, or in a peptide subunit thereof, by conversion of a suitable precursor therefor. Thus the arginyl and homoarginyl radicals may readily be formed by guanidation of an ornithyl or lysyl radical respectively, using a reagent such as 1-guanyl-3,5-dimethylpyrazole. The pyroglutamyl radical may be formed by cyclisation of a glutamyl or glutaminyl radical which may itself be introduced in a suitably protected form into the polypeptide or a subunit thereof and deprotected prior to the cyclisation step, as described in for example J. Med. Chem., 14 (1971) 469; Helv. Chim. Acta., 53 (1970) 63; Biochem. Biophys. Res. Comm., 45 (1971) 767,822; and Chem. Berichte, 105 (1972) 2872.

Those compounds of formula (I) wherein $X^1$ is the group $V^1$—Pro— as herein defined may be prepared via an initially formed intermediate peptide with the appropriate group W at the C-terminal position and at the N-terminal end a group $V^3$—Pro— where $V^3$ is a protecting (masking) group outside the scope of $V^1$ as defined in formula (I). Conversion of this intermediate to the desired end-product may be effected by selective removal of the group $V^3$ and selective reprotection of the N-terminal prolyl radical with the desired group $V^1$, using techniques well-established in the art. It will be appreciated that in an analogous manner a compound of formula (I) wherein $X^1$ is a group $V^1$—Pro— as herein defined may be converted to an analogue thereof also within formula (I) wherein $V^1$ is a different group.

Depending upon the reaction conditions, the compounds of formula (I) are obtained in the form of the free bases (peptides) or the acid additional salts thereof. The acid additional salts may be converted into the free bases or salts of other acids, and the bases may be converted into acid addition salts thereof, by techniques well known in the art.

The compounds of formula (I) wherein $X^2$ is histidyl form complexes with pharmaceutically acceptable metals such as zinc, and such complexes exhibit a prolonged period of action in vivo upon parenteral administration as compared with the uncomplexed peptides and their acid addition salts. Such complexes may be prepared by techniques analogous to those well known in the art and as taught in, for example, published South African patent specification No. 73/2419. Thus the zinc complexes may be prepared by, for example, dissolving the peptide in an aqueous solution containing excess zinc ions and optionally also phosphate ions and adjusting the pH with dilute alkali metal hydroxide solution, the complex being then precipitated. The zinc ions may be derived from an ionizable zinc compound such as the chloride or sulphate and the phosphate ions, when present, may be derived from an alkali metal phosphate such as disodium hydrogen phosphate.

The peptides of formula (I), their acid addition salts and their complexes with pharmaceutically acceptable metals may thus be prepared by condensing a reagent (II)

$$Y^1\text{—OH} \quad (II)$$

wherein $Y^1$ is selected from (i) a group $X^1$ as above defined, (ii) a group cyclisable to pyroglutamyl, (iii) the prolyl radical, and (iv) a partial radical sequence having one of the groups (i), (ii) and (iii) herein recited at its N-terminal end and from thereon corresponding to the product peptide above defined, with a reagent (III)

$$H\text{—}Y^2 \quad (III)$$

wherein $Y^2$ corresponds to the balance of the above defined product peptide, the reagents $Y^1$—OH and H—$y^2$ being optionally protected and/or activated where and as appropriate and wherein in the groups $Y^1$ and $Y^2$ thereof, as appropriate, any arginyl or homoarginyl radical present in the above defined product peptide is optionally replaced by respectively an ornithyl or lysyl radical, followed if necessary and as appropriate by one or more of the steps of deprotection of the product, cyclisation of the N-terminal group thereof to the pyroglutamyl radical or protection of the N-terminal group with a group $V^1$ as above defined, guanidation of any ornithyl or lysyl radical therein to the arginyl or homoarginyl radical respectively, conversion of the product into the peptide or an acid addition salt thereof, and complexing of the peptide with a pharmaceutically acceptable metal.

In the selection of peptide subunits for synthesis prior to a final condensation step it is common practice to have regard to the following factors. (i) To minimise racemisation, fragments having C-terminal glycyl are advantageous. (ii) Fragments having very low solubility in the solvents normally used in peptide synthesis are disadvantageous. (iii) It is advantageous if the fragments are crystalline. (iv) Fragments having N-terminal tryptophyl are advantageous, as by incorporating tryptophyl as the final N-terminal residue of the fragment, prolonged working with this labile radical is avoided.

With regard to the compounds of formula (I) the reagent $Y^1$—OH identified above preferably corresponds to (a) the fragment $X^1$—$X^2$—$X^3$—$X^4$—$X^5$—$X^6$; (b) the fragment $X^1$—$X^2$; or (c) the fragment $X^1$ of the product peptide, the reagent H—$Y^2$ being chosen appropriately.

Because of their LH-RH antagonist activity, as above defined and described, the peptides of formula (I), their pharmaceutically acceptable acid addition salts and their complexes with pharmaceutically acceptable metals may be used in the treatment of mammals in the fields of both human and veterinary medicine in conditions where it is desirable to limit the effect on the anterior pituitary of endogenous LH-RH and thus limit the release therefrom of the gonadotrophins LH and FSH. Specifically such peptides, salts and complexes have utility, in both human and veterinary medicine, in (i) the therapy of conditions in which there is hypersecretion of LH-RH and/or of LH and FSH, and (ii) in the regulation of ovulation and in the male by the regulation of maturation of spermatozoa.

It will be apparent that quite apart from their value in human medicine these peptides, salts and complexes are of particular value in enabling contraception in domestic mammals such as cats and dogs.

For each of the utilities mentioned above the amount required of the peptide, salt thereof or complex thereof (hereinafter referred to as the active ingredient) will of course vary both with the particular active ingredient and with the route of administration. In general however for each of these utilities the dosage for nasal or parenteral administration will be in the range 0.005 to 200 μg per kg bodyweight of mammal, preferably 0.01 to 100 μg, and optimally 0.02 to 10 μg/kg; for oral or vaginal administration the dosage will generally be in the range 0.005 to 1000 μg/kg, preferably 0.05 to 200 μg/kg, and optimally 0.2 to 50 μg/kg (all dosages calculated with reference to the base (peptide)).

While it is possible for the active ingredients to be administered as the raw chemical it is preferable, in view of their potency, to present them as a pharmaceutical formulation preparation.

The formulations, both veterinary and for human use, of the present invention comprise an active ingredient, as above defined, together with one or more acceptable carriers therefor and optionally other therapeutic ingredients. The carrier(s) must be "acceptable" in the sense of being compatible with the other ingredients of the formulation and not deleterious to the recipient thereof. Desirably the formulations should not include oxidising agents and other substances with which peptides are known to be incompatible.

The formulations include those suitable for oral, rectal, nasal, topical (buccal), vaginal or parenteral (including subcutaneous, intramuscular and intravenous) administration, although the most suitable route in any given case will depend upon the active ingredient. As another possibility an active ingredient may be presented as a depot formulation having slow-release characteristics suiting it for implantation in the body of the recipient, for example sub-cutaneously, intraperitoneally or intravaginally. The formulations may conveniently be presented in unit dosage form and may be prepared by any of the methods well known in the art of pharmacy. All methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product into the desired formulation.

Formulations of the present invention suitable for oral administration may be presented as discrete units such as capsules, cachets or tablets each containing a predetermined amount of the active ingredient; as a powder or granules; or as a solution or a suspension in an aqueous liquid or a non-aqueous liquid; or as an oil-in-water liquid emulsion or a water-in-oil liquid emulsion. The active ingredient may also be presented as a bolus, electuary or paste.

A tablet may be made by compression or moulding, optionally with one or more accessory ingredients. Compressed tablets may be prepared by compressing in a suitable machine, the active ingredient in a free-flowing form such as a powder or granules, optionally mixed with a binder, lubricant, inert diluent, lubricating, surface active or dispersing agent. Moulded tablets may be made by moulding in a suitable machine, a mixture of the powdered compound moistened with an inert liquid diluent.

Formulations for rectal administration may be presented as a suppository with the usual carriers such as cocoa butter, while a suitable formulation for nasal administration is nasal drops comprising the active ingredient in aqueous or oily solution.

Formulations suitable for topical administration in the mouth include lozenges comprising the active ingredient in a flavoured basis, usually sucrose and acacia or tragacanth; and pastilles comprising the active ingredient in an inert basis such as gelatin and glycerin, or sucrose and acacia.

Formulations suitable for vaginal administration may be presented as pessaries, creams, pastes or spray formulations containing in addition to the active ingredient such carriers as are known in the art to be appropriate.

Formulations suitable for parenteral administration conveniently comprise sterile aqueous solutions of the active ingredient, which solutions are preferably isotonic with the blood of the recipient. Such formulations may be conveniently prepared by dissolving solid active ingredient in water to produce an aqueous solution, and rendering said solution sterile and isotonic with the blood of the recipient.

A suitable slow-release medium for a depot formulation is polyethylene glycol.

It should be understood that in addition to the aforementioned ingredients the formulations of this invention may include one or more additional ingredients such as diluents, buffers, flavouring agents, binders, surface active agents, thickeners, lubricants, preservatives (including anti-oxidants) and the like.

Where the formulation, for human or for veterinary use, is presented in unit dosage form, for example those unit dosage forms specifically mentioned above, each unit thereof conveniently contains the active ingredient (as above defined) in the following amounts, all references being to the base (peptide). For nasal or parenteral administration: 0.25 μg to 10 mg, preferably 0.5 μg to 5 mg, and optimally 1.0 μg to 500.0 μg. For oral or vaginal administration: 0.25 μg to 50 mg, preferably 2.5 μg to 10 mg, and optimally 10 μg to 2.5 mg.

It will be appreciated from the foregoing that what we will claim comprise any novel feature described herein, principally and not exclusively, for example:

a. The peptides of formula (I) as above defined, their acid addition salts and their complexes with pharmaceutically acceptable metals.

b. Methods for the preparation of the peptides, salts and complexes as described above.

c. Pharmaceutical formulations comprising a peptide of formula (I), a pharmaceutically acceptable acid addition salt thereof or a complex thereof with a pharmaceutically acceptable metal, together with an acceptable carrier therefor.

d. Methods for the preparation of the pharmaceutical formulations defined in (c) above.

e. A method of contraception in a mammal which comprises the administration to the mammal of a peptide of formula (I), a pharmaceutically acceptable acid addition salt thereof or a complex thereof with a pharmaceutically acceptable metal.

f. A method for the regulation of ovulation (in a female mammal) or for the regulation of maturation of spermatozoa (in a male mammal) which comprises the administration to the mammal of a peptide of formula (I), a pharmaceutically acceptable acid addition salt thereof or a complex thereof with a pharmaceutically acceptable metal.

The following Examples serve to illustrate the present invention but should not be construed as in any way providing a limitation thereof. All temperatures are in degrees Celsius.

Example 1

Preparation of the compound (A)

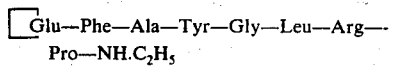

This was prepared according to the scheme set out in the accompanying Table 1, wherein Z = benzyloxycarbonyl
BOC = t-butyloxycarbonyl
Bu$^t$ = t-butyl
Et = ethyl The protected dipeptide (1) was obtained by coupling equimolar amounts of benzyloxycarbonylglycine and leucine t-butyl ester in methylene dichloride, in the presence of one equivalent of dicyclohexylcarbodiimide. After an initial 30 minute period at −10° C, the reaction mixture was stirred at 4° C for 24 hrs. Following the removal of the dicyclohexylurea, the reaction mixture was worked up to yield the dipeptide in 94% yield. The protected dipeptide was dissolved in methanol and after flushing with nitrogen, 10% palladium on charcoal catalyst was introduced. Hydrogen was passed through the stirred mixture for 20 hrs at room temperature. After removal of the catalyst, the solution was worked up to yield the partially deprotected dipeptide (1a).

The conversion of (1a) to the protected hexapeptide (II) proceeded by the stepwise addition of the appropriate Z- protected amino acids and subsequent removal of the amino protecting group by hydrogenolysis. Practical details of the coupling and deprotection steps are essentially as for those described above for the dipeptide. Peptide (III) was obtained by treatment of (II) with trifluoroacetic acid in the presence of a large excess of anisole for 1 hour at room temperature. Evaporation of the reaction mixture and precipitation with ether gave the desired product.

The ethylamide of Z—Pro—OH was prepared by a mixed anhydride coupling between Z—Pro—OH and ethylamine. Coupling of BOC(NO$_2$)—Arg—OH with H—Pro—NH.C$_2$H$_5$ resulted in a mixture of the desired protected peptide and the lactam of BOC(NO$_2$)—Arg—OH which was resolved by exhaustive extraction with water of the slightly more hydrophilic dipeptide from an ethyl acetate solution of the mixture. The peptide was obtained by lyophilisation of the aqueous extracts; it was pure by thin layer chromatography and had the correct elemental analysis. The peptide was deprotected with N-hydrogen chloride in acetic acid to yield (IV) which was then coupled with (III) in dimethylformamide in the presence of dicyclohexylcarbodiimide and one equivalent of 1-hydroxybenzotriazole.

The nitro group of (V) was removed by hydrogenolysis in the solvent mixture methanol: acetic acid: water, 5 : 1 : 1. 350 mg of palladium/charcoal catalyst was used for each millimole of peptide, and hydrogen was passed through the stirred suspension for 24 hrs. Purification of the product, first by dry-column chromatography on silica gel, and then by gradient elution chromatography on carboxymethyl cellulose yielded the peptide (A) (as the acetate addition salt) in pure form.

(A) was positive to Pauly reagent (for deprotected tyrosine) and Sakaguchi reagent (for deprotected arginine). It behaved as an essentially single component in thin layer chromatography with each of the following solvent systems:
 a. Chloroform: methanol: 0.880 ammonia, 60:45:20
 b. Chloroform: methanol: 32% acetic acid, 60:45:20
 c. n-Butanol: acetic acid: water: ethylacetate, 1:1:1:1
Amino acid ratios, after hydrolysis in 6N hydrochloric acid for 24 hrs at 110° C, were:
 Glu: 1.08, Phe: 0.99, Ala: 1.00, Tyr: 0.98
 Gly: 0.99, Leu: 1.00, Arg: 0.91, Pro: 0.98
 Recovery 95% (calculated as the acetate)

Characterising data $\{\alpha\}_D^{26} - 65.4°$ (C = 0.785, 1% acetic acid)
Ultra-violet absorption spectrum (in 0.1N sodium hydroxide):
$E_{242}$ : 11260, $E_{293}$ : 2370

AMT-Me = 1-methyl-5-aminomethyl tetrazole

1-Methyl-5-aminomethyl tetrazole hydrochloride was coupled with the p-nitrophenyl ester of benzyloxycarbonyl proline in dimethylformamide in the presence of one equivalent of triethylamine. The reaction mixture was stirred at room temperature overnight and then worked up to yield a crystalline product which melted at 91°-92° C. The benzyloxycarbonyl group was removed by hydrogenolysis, and the resulting $N^5$-propyl-(1-methyl-5-aminomethyl) tetrazole was coupled with

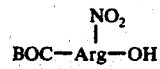

TABLE 1

| Glu | Phe | Ala | Tyr | Gly | Leu | Arg | Pro |
|---|---|---|---|---|---|---|---|
| | | | Z—OH | H——OBu' | | | |
| | | | Z— | (1) ——OBu' | | | |
| | | Z—OH | H— | (1a) ——OBu' | | | |
| | | Z— | | ——OBu' | | | |
| | Z—OH | H— | | | ——OBu' | | |
| | Z— | | | | ——OBu' | | |
| Z—OH | H— | | | | ——OBu' | Z—OH | |
| Z— | | | | | ——OBu' | Z—NH.Et (NO₂) | |
| —OH | H— | | | | ——OBu' | BOC—OH (NO₂) H—NH.Et | |
| | | | | (II) ——OBu' | BOC—(NO₂) | —NH.Et |
| | | | (III) | —OH | H—(IV) (NO₂) —NH.Et | |
| | | | (V) | | | —NH.Et |
| | | | (A) | | | —NH.Et |

TABLE 2

| Arg | Pro |
|---|---|
| | Z—OH |
| Z—(NO₂) | —AMT—Me |
| BOC—OH (NO₂) | H—AMT—Me |
| BOC—(NO₂) (I) | —AMT—Me |
| H— (II) | —AMT—Me |

Example 2

Preparation of the Compound (B)

⌐Glu—Phe—Ala—Tyr—Gly—Leu—Arg—Pro—1-methyl-5-aminomethyl tetrazole

The hexapeptide, ⌐Glu—Phe—Ala—Tyr—Gly—Leu—OH, was prepared as described in Example 1. The C-terminal fragment was prepared according to the scheme set out in the accompanying Table 2, wherein:
 Z = benzyloxycarbonyl
 BOC = t-butyloxycarbonyl in dimethylformamide, using the carbodiimide method. This reaction was accompanied by lactam formation as described in Example 1, and separation of the required product from the contaminating lactam was achieved by a method of extraction similar to that described in Example 1. Lyophilisation of the aqueous extracts gave a product (I) which was pure by thin layer chromatography and had the correct elemental analysis. After deprotection with anhydrous hydrogen chloride in acetic acid, the dipeptide (II) was coupled with the hexapeptide by the carbodiimide/hydroxy benzotriazole method. The nitro protecting group was removed from the arginine residue by prolonged hydrogenation in methanol, acetic acid and water mixture. The final product (B) was then purified by chromatographic methods as described in Example 1.

The purified material (as the acetate addition salt) gave a positive reaction to Pauly reagent and also to Sakaguchi reagent. It was essentially pure when examined by thin layer chromatography in the three systems previously described in Example 1.
 Amino acid ratios after acid hydrolysis were:
 Glu: 1.08, Phe: 1.01, Ala: 1.02, Tyr: 0.97
 Gly: 1.00, Leu: 1.00, Arg: 1.01, Pro: 0.97
 Recovery 83% (calculated as the acetate)

Ultra-violet absorption spectrum (in 0.1N sodium hydroxide)

$E_{242}$: 9940, $E_{293}$: 2060

$[\alpha]_D^{26} - 61.4°$ (C = 1, 1% acetic acid)

Example 3

Preparation of the compound (C)

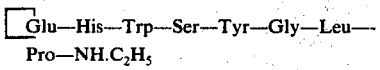
Pro—NH.C$_2$H$_5$

Starting with the compound H—Gly—OCH$_3$, the protected tetrapeptide Z—Trp—Ser(Bzl)—Tyr(Bzl)—Gly—OCH$_3$ was prepared by a series of carbodiimide mediated couplings, and then saponified in aqueous dioxan to give the corresponding free acid which crystallised from ethanol as fine needles, m.p. 202°–204° C. The acid was coupled with H—Leu—OBu$^t$ (carbodiimide/benzotriazole) to give a product which crystallised from aqueous methanol, m.p. 158°–160° C.

Deprotection in trifluoroacetic acid/anisole gave Z—Trp—Ser(Bzl)—Tyr(Bzl)—Gly—Leu—OH, m.p. 144°–145° C from methanol/ether, which was coupled with H—Pro—NH.C$_2$H$_5$ (carbodiimide/benzotriazole). Hydrogenation of the product in the presence of palladium on charcoal catalyst gave the completely deprotected hexapeptide which was then coupled with ⌐Glu—His—OH in aqueous dimethylformamide (carbodiimide/benzotriazole) to yield crude (C). The crude product was chromatographed first on silica gel (chloroform: methanol: acetic acid) and then on carboxymethylcellulose to give the pure octapeptide (as the acetate addition salt which ran as a single component on thin layer chromatography with each of the three solvent systems detailed in Example 1 and was positive to Pauly reagent (for deprotected tyrosine)and to Ehrlich reagent (for tryptophan).

In the foregoing, Z and Bu$^t$ have the meanings defined in Example 1 and Bzl is the benzyl group.

Amino acid ratios, after hydrolysis as in Example 1:
Glu: 1.09 His: 1.01 Ser: 0.85 Tyr: 0.96
Gly: 1.02 Leu: 1.00 Pro: 0.96
Recovery: 91% (calculated as the acetate)
Optical rotation: $\{\alpha\}_D^{23} - 44.65°$ (C = 1, 1% acetic acid)

Example 4

Preparation of the compound (D)

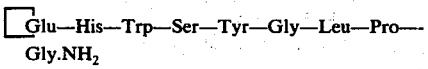
Gly.NH$_2$

The protected pentapeptide Z—Trp—Ser(Bzl)—Tyr(Bzl)—Gly—Leu—OH (prepared as in Example 3) was coupled with H—Pro—Gly.NH$_2$ (carbodiimide/benzotriazole in dimethylformamide) and the resulting protected heptapeptide then hydrogenated to give H—Trp—Ser—Tyr—Gly—Leu—Pro—Gly—NH$_2$. This was coupled with ⌐Glu—His—OH (carbodiimide/benzotriazole in aqueous dimethylformamide) to yield crude (D) which was then purified by dry column chromatography on silica gel using the solvent mixture chloroform: methanol: 32% acetic acid, 60:45:20. Further purification was obtained by chromatography on carboxymethylcellulose.

The pure nonapeptide, as the acetate addition salt, was Pauly and Ehrlich positive and ran as a single component on thin layer chromatography in each of the three solvent systems detailed in Example 1.

Amino acid ratios, after hydrolysis as in Example 1.
Glu: 1.07 His: 1.01 Ser: 0.84 Tyr: 0.95
Gly: 2.00 Leu: 1.00 Pro: 0.94
Recovery: 86% (calculated as the acetate)
Optical rotation: $[\alpha]_D^{23} - 43.54°$ (C = 1, 1% acetic acid)

Example 5

Preparation of the compounds

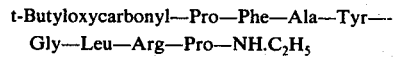  (E)

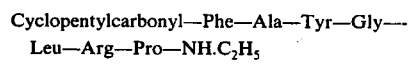  (F)

In the following BOC— represents the t-butyloxycarbonyl group and Bzl— represents the benzyl group.

The syntheses of compounds (E) and (F) both proceeded from the common precursor BOC—Arg(NO$_2$)—Pro—NH.C$_2$H$_5$ (Example 1). In each case the remaining coupling steps were carried out using the Repetitive Excess Mixed Anhydride (R.E.M.A.) procedure described by Tilak (Tetrahedron Letters, 849 (1970)) and by Beyerman (Helv. Chim. Acta., 56, 1729 (1973)). Each intermediate step was checked for purity by thin layer chromatography. The tyrosine residue in each compound was incorporated as BOC—Tyr(Bzl)—OH, and careful washing was required to remove the excess of this compound from the isolated peptide.

As the initial step in the synthesis of compound (E), 6.76 millimoles of

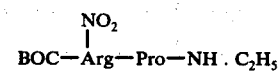

were deprotected by treatment with 40 mls of N-hydrogen chloride in acetic acid for 45 minutes at room temperature. The reaction mixture was concentrated at 30° C, the residue triturated with ether, filtered and then dried thoroughly over phosphorus pentoxide and sodium hydroxide pellets. The deprotected dipeptide hydrochloride thus obtained, was dissolved in 18 mls dimethylformamide and treated with 6.76 millimoles of N-methyl morpholine dissolved in 4 mls dimethylformamide; and the solution then cooled to −15° C. 10.15 Millimoles of t-butyloxycarbonyl leucine monohydrate were dissolved in 15 mls tetrahydrofuran and treated with 10.15 millimoles of N-methyl morpholine in 3 mls tetrahydrofuran. This solution was cooled to −15° C, and a solution of 9.46 millimoles of isobutylchloroformate in 3 mls tetrahydrofuran was added with vigorous stirring. After 2 minutes at −15° C the cooled solution of the amino component described above, was added to the mixed anhydride, and the components were allowed to react at −15° C for 2½ hours. The temperature was then raised to 0° C and 10 mls of 2M potassium bicarbonate solution were run in to decompose the excess mixed anhydride. The resultant mixture was poured onto 300 mls of ice-cold 75% saturated sodium chloride solution, and the precipitated oil taken up into ethyl acetate. The organic layer was washed with sodium chloride solution, dried and concentrated to dryness in vacuo. After trituration with ether, the pure protected peptide BOC—Leu—Arg(NO$_2$)—Pro—NH.C$_2$H$_5$ was obtained (in 88% yield).

By a series of alternate deprotections and excess mixed anhydride couplings with the appropriate protected amino acids using the conditions described above there was prepared the protected octapeptide

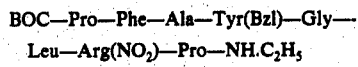

This was hydrogenated in a methanol: acetic acid: water mixture (palladium/charcoal catalyst) to yield crude (E) which was purified chromatograhically. The pure product (as the acetate addition salt) ran as a single component on thin layer chromatography with each of the three systems detailed in Example 1.

Amino acid ratios, after hydrolysis as in Example 1:
Pro: 1.73; Phe: 0.97; Ala: 0.96; Tyr: 0.97
Gly: 0.99; Leu: 1.00; Arg: 0.94

Optical rotation: $[\alpha]_D^{23} - 72.2°$ (C = 1, 1% acetic acid)

Compound (F) was prepared in the same manner as above described for compound (E), except that cyclopentane carboxylic acid was used for the final coupling. The crude product was purified chromatographically on carboxymethyl cellulose. The pure material (as the acetate addition salt) ran as a single component in each of the three systems detailed in Example 1.

Amino acid ratios, after hydrolysis as in Example 1:
Phe: 0.96; Ala: 0.97; Tyr: 0.97; Gly: 0.97
Leu: 1.00; Arg: 1.00; Pro: 0.97

Optical rotation: $[\alpha]_D^{23} - 54.52°$ (C = 1, 1% acetic acid)

Examples of Pharmaceutical Formulations (i) Tablets (composition per tablet)

| | | | |
|---|---|---|---|
| Compound of formula (I) | 1.0 mg | 5.0 mg | 25.0 mg |
| Starch | 20.0 mg | 20.0 mg | 20.0 mg |
| Lactose | 50.0 mg | 50.0 mg | 50.0 mg |
| Polyvinylpyrrolidone | 8.0 mg | 8.0 mg | 8.0 mg |
| Magnesium stearate | 2.0 mg | 2.0 mg | 2.0 mg |

The compound of formula (I) was intimately mixed with the starch and the lactose, and the mixture granulated using a solution of the polyvinylpyrrolidone in water. The granules were then dried, the magnesium stearate added, and tablets prepared by compression.

(ii) Pessaries (composition per pessary)

| | | | |
|---|---|---|---|
| Compound of formula (I) | 0.5 mg | 2.5 mg | 12.5 mg |
| Theobroma oil | 1.0 g | 1.0 g | 1.0 g |

The compound of formula (I) was mixed into a smooth paste with a little of the melted theobroma oil at a temperature not exceeding 45° C. The paste was then incorporated into the remaining melted oil and the mixture poured into sitable lubricated moulds and allowed to set.

(iii) Vaginal tablets (composition per tablet)

| | | | |
|---|---|---|---|
| Compound of formula (I) | 0.5 mg | 2.5 mg | 12.5 mg |
| Lactose | 500.0 mg | 500.0 mg | 500.0 mg |
| Starch | 450.0 mg | 450.0 mg | 450.0 mg |
| Polyethylene glycol 6000 | 100.0 mg | 100.0 mg | 100.0 mg |
| Magnesium stearate | 10.0 mg | 10.0 mg | 10.0 mg |

The compound of formula (I) was intimately mixed with the starch and the lactose and the mixture granulated using a solution of the polyethylene glycol 6000 in water. The granules were dried, the magnesium stearate added, and tablets formed by compression in a suitably shaped tablet die.

(iv) Injection solutions

| | | | |
|---|---|---|---|
| Compound of formula (I) | 0.04 g | 0.2 g | 1.0 g |
| Dilute acetic acid | sufficient to produce pH 3.0–4.0 | | |
| Chlorocresol | 0.1 g | 0.1 g | g |
| Water for injections | to 100.0 ml | | |

The compound of formula (I) was dissolved in 9/10 of the final volume of water adjusted to pH 3.0–4.0 with dilute acetic acid. The chlorocresol was then added and dissolved, and the mixture diluted to volume with the remaining water. The solution was sterilized by passage through a membrane filter, 0.22μm pore size, and then distributed aseptically into 10 ml vials. The vials were each closed with a sterile rubber stopper which was secured with an aluminium collar.

The three solutions detailed above contained respectively 0.4 mg, 2 mg, and 10 mg per ml of the compound of formula (I).

In the above the compound of formula (I) is the end-product of the foregoing Example 1 in the form of the acetate addition salt thereof, although all quantities thereof are calculated with respect to the base (peptide).

What we claim is:
1. Glu—Phe—Ala—Tyr—Gly—Leu—Arg—Pro—ethylamide or an acid addition salt thereof, wherein all residues are those of the L-amino acids except in the case of glycine.
2. Glu—Phe—Ala—Tyr—Gly—Leu—Arg—Pro—1-methyl-5-amino-methyltetrazole or an acid addition salt thereof, wherein all residues are those of the L-amino acids except in the case of glycine.
3. Glu—His—Trp—Ser—Tyr—Gly—Leu—Pro—ethylamide or an acid addition salt thereof, wherein all residues are those of the L-amino acids except in the case of glycine.
4. Glu—His—Trp—Ser—Tyr—Gly—Leu—Pro—glycine amide or an acid addition salt thereof, wherein all residues are those of the L-amino acids except in the case of glycine.
5. t-Butyloxycarbonyl—Pro—Phe—Ala—Tyr—Gly—Leu—Arg—Pro—ethylamide or an acid addition salt thereof, wherein all residues are those of the L-amino acids except in the case of glycine.
6. Cyclopentylcarbonyl—Phe—Ala—Tyr—Gly—Lue—Arg—Pro—ethylamide or an acid addition salt thereof, wherein all residues are those of the L-amino acids except in the case of glycine.

* * * * *